(12) United States Patent
Maetzler et al.

(10) Patent No.: US 11,709,172 B2
(45) Date of Patent: *Jul. 25, 2023

(54) METHOD FOR OPERATING A LABORATORY SYSTEM

(71) Applicant: Roche Diagnostics Operations, Inc., Indianapolis, IN (US)

(72) Inventors: Marco Maetzler, Belmont, CA (US); Christopher Schofield, Rotkreuz (CH); Ole Lambaek, Cham (CH); Moritz von Hopffgarten, Heidelberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 170 days.

This patent is subject to a terminal disclaimer.

(21) Appl. No.: 17/120,874

(22) Filed: Dec. 14, 2020

(65) Prior Publication Data

US 2021/0140987 A1    May 13, 2021

Related U.S. Application Data

(63) Continuation of application No. 15/986,210, filed on May 22, 2018, now Pat. No. 10,895,580.

(30) Foreign Application Priority Data

May 29, 2017    (EP) .................................... 17173241

(51) Int. Cl.
    *G01N 35/00*    (2006.01)
    *G01N 35/10*    (2006.01)
    (Continued)

(52) U.S. Cl.
    CPC ........ *G01N 35/00871* (2013.01); *B01L 3/021* (2013.01); *G01N 35/0095* (2013.01);
    (Continued)

(58) Field of Classification Search
    CPC ............ G01N 2035/0094; G01N 2035/00881; G01N 35/00871; G01N 35/00732;
    (Continued)

(56) References Cited

U.S. PATENT DOCUMENTS

| | | | |
|---|---|---|---|
| 6,581,012 B1 * | 6/2003 | Aryev | G01N 35/0092 702/22 |
| 7,647,190 B2 | 1/2010 | Uemura et al. | |
| 7,754,149 B2 | 7/2010 | Sugiyama | |
| 2002/0147515 A1 * | 10/2002 | Fava | G01N 35/0092 700/95 |

(Continued)

FOREIGN PATENT DOCUMENTS

| | | |
|---|---|---|
| EP | 2450711 A1 | 1/2013 |
| JP | 2012-037346 A | 2/2012 |
| WO | 2008/150735 A1 | 12/2008 |
| WO | 2010/106885 A1 | 9/2010 |

*Primary Examiner* — Shogo Sasaki
(74) *Attorney, Agent, or Firm* — Roche Diagnostics Operations, Inc.

(57) ABSTRACT

A method for operating a laboratory system comprising instruments for processing samples and a control unit connected by a communication network is presented. The method comprises receiving and identifying a biological sample and retrieving an order list from a database. The list comprises a plurality of targets defining one or more processing steps to be carried out on the biological sample by one or more of the laboratory instruments. The method also comprises selecting a workflow strategy and retrieving workflow acceptance criterion corresponding to the workflow strategy. The control unit determines a sample workflow for processing the sample based on the workflow strategy and determines whether the sample workflow satisfies the workflow acceptance criterion. If the sample workflow does not satisfy the workflow acceptance criterion, workflow strategy and the workflow acceptance criterion is refined and the sample workflow is determined again until it satisfies the workflow acceptance criterion.

21 Claims, 4 Drawing Sheets

(51) Int. Cl.
  *B01L 3/02* (2006.01)
  *G16H 10/40* (2018.01)
(52) U.S. Cl.
  CPC .............. *G01N 35/00722* (2013.01); *G01N 35/1016* (2013.01); *G16H 10/40* (2018.01); *B01L 2200/14* (2013.01); *G01N 2035/009* (2013.01); *G01N 2035/00881* (2013.01)
(58) Field of Classification Search
  CPC .......... G01N 35/0095; G01N 35/1016; G01N 2035/009; G01N 35/00722; G01N 2035/00831; G01N 35/0092; B01L 2200/14; B01L 3/021; G16H 10/40
  See application file for complete search history.

(56) References Cited

U.S. PATENT DOCUMENTS

| | | | |
|---|---|---|---|
| 2007/0196909 A1* | 8/2007 | Showalter | G06Q 10/06 435/283.1 |
| 2007/0282476 A1* | 12/2007 | Song | G06Q 10/1095 700/100 |
| 2008/0235055 A1* | 9/2008 | Mattingly | G06Q 10/10 705/3 |
| 2009/0130765 A1 | 5/2009 | Bauer et al. | |
| 2012/0109531 A1* | 5/2012 | Knafel | G01N 35/00871 702/19 |
| 2013/0111978 A1 | 5/2013 | Mizumoto et al. | |
| 2013/0128035 A1 | 5/2013 | Johns et al. | |
| 2015/0031143 A1 | 1/2015 | Suzuki et al. | |
| 2015/0242395 A1 | 8/2015 | Hodak | |

\* cited by examiner

METHOD FOR OPERATING A LABORATORY SYSTEM

CROSS-REFERENCE TO RELATED APPLICATIONS

This application is a continuation of U.S. application Ser. No. 15/986,210, filed May 22, 2018, now U.S. Pat. No. 10,895,580, which claims the benefit of EP 17173241.5, filed May 29, 2017, which is hereby incorporated by reference.

BACKGROUND

The present disclosure relates to a computer-implemented method for operating a laboratory system for processing biological samples and to a laboratory system for processing biological samples.

In vitro diagnostic testing has a major effect on clinical decisions, providing physicians with pivotal information.

In analytical laboratories, in particular clinical laboratories, a multitude of analyses on samples are executed by an analytical system in order to determine the physiological state of a patient. The kind of analytical test to be executed on a biological sample is typically specified as a target, which is typically registered in a laboratory information system as a test order and sent to the laboratory system.

According to established laboratory procedures, when a biological sample is received, it is first identified—for example, by an identifier label and corresponding label reader such as a barcode label and barcode reader. Once the biological sample is identified, an order list is retrieved from a database comprising a plurality of targets, each target defining one or more processing steps to be carried out on the biological sample by one or more of the laboratory instruments. These processing steps may be pre-analytical processing steps such as aliquoting, sample preparation, analytical processing steps such as an assay to determine the presence and/or concentration of an analyte in the biological sample, or post-analytical processing steps such as archiving of the biological sample. Before the biological sample can be processed by the various laboratory instruments of the laboratory system, a sample workflow is determined. The sample workflow is defined from one or more from the list comprising: a number of aliquots to be prepared from the biological sample; an allocation of an aliquot of the biological sample to each target; a sequence in which the targets are to be processed and/or a timing of processing of the targets.

Solutions for control units are known (such as the cobas IT middleware, cobas Infinity or cobas IT 3000 products of Roche Diagnostics) which determine a sample workflow for each biological sample received and identified. Such known control units determine the sample workflow based on a workflow strategy, which defines one or more priority rules in processing the biological sample. As an example, for a particular laboratory, fastest processing time (turn-around-time (TAT)) is of highest priority. In this case, the workflow strategy will prioritize the creation of several aliquots of the biological sample in order to allow parallel processing of the aliquots on several instruments at the same time. In order to validate a sample workflow, a workflow acceptance criterion is defined comprising one or more workflow evaluation rule(s). One common workflow evaluation rule is determining whether an estimate of the total required sample volume is lower than or equal to the available sample volume of the biological sample. If the sample workflow satisfies the workflow acceptance criterion, the laboratory instruments are instructed by the control unit to process the biological sample according to the sample workflow. However, if the sample workflow does not satisfy the workflow acceptance criterion, known solutions merely raise an error message indicative that the sample workflow did not satisfy the workflow acceptance criterion. Optionally, in certain cases, the biological sample is sorted to a so-called error target for an operator to manually handle such samples.

This is however disadvantageous, as manual intervention is required, which may be time consuming, error prone, increase staff load and require constant supervision of the laboratory—which is not desired, especially overnight.

Therefore, there is a need for a method for operating a laboratory system, respectively a laboratory system configured to carry out such method, which enables automated handling of biological samples, improving the way a control unit determines workflows for processing biological samples in order to prevent user errors, decrease staff load and avoid the need for constant supervision.

SUMMARY

According to the present disclosure, a computer implemented method for operating a laboratory system, wherein the laboratory system comprises a plurality of laboratory instruments for processing biological samples and a control unit communicatively connected by a communication network, is presented. The method can comprise receiving and identifying a biological sample by one of the plurality of laboratory instruments and retrieving an order list from a database by the control unit. The list can comprise a plurality of targets corresponding to the biological sample. Each target can define at least one processing steps to be carried out on the biological sample by at least one of the plurality of the laboratory instruments. The method can also comprise selecting a workflow strategy by the control unit. The workflow strategy can define at least one-priority rules in processing the biological sample. The method can also comprise retrieving workflow acceptance criterion by the control unit from a database corresponding to the workflow strategy, determining a sample workflow by the control unit for processing the biological sample based on the workflow strategy and the order list, determining by the control unit whether the sample workflow satisfies the workflow acceptance criterion, and, if the sample workflow does not satisfy the workflow acceptance criterion, refining workflow strategy by the control unit, refining workflow acceptance criterion by the control unit, and determining the sample workflow by the control unit based on the workflow strategy and the order list until the sample workflow satisfies the workflow acceptance criterion.

Accordingly, it is a feature of the embodiments of the present disclosure to provide for a method for operating a laboratory system, respectively a laboratory system configured to carry out such method which enables automated handling of biological samples, improving the way a control unit determines workflows for processing biological samples in order to prevent user errors, decrease staff load and avoid the need for constant supervision. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1A:
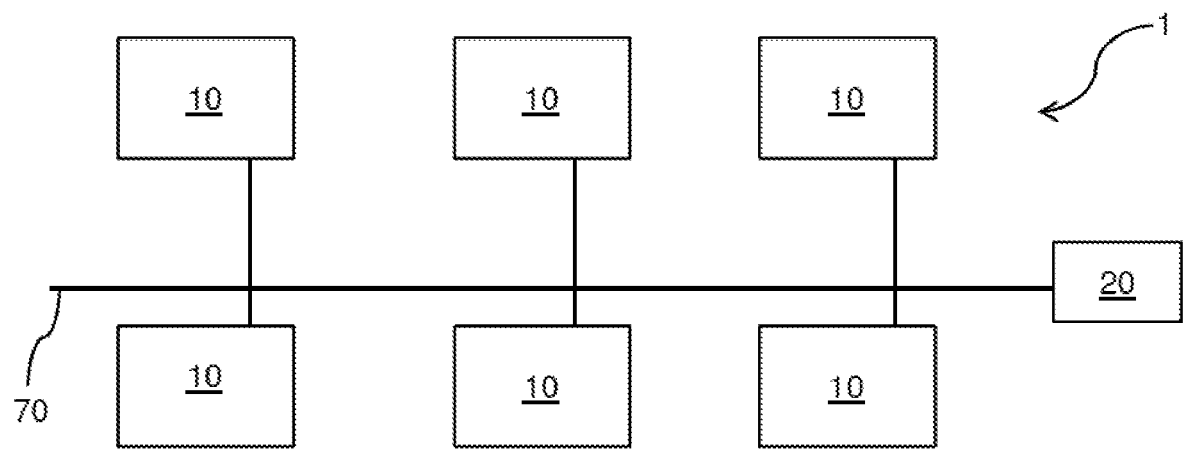
FIG. 1A illustrates a highly schematic block diagram according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The term 'laboratory instrument' as used herein can encompass any apparatus or apparatus component operable to execute one or more processing steps/workflow steps on one or more biological samples. The expression 'processing steps' thereby can refer to physically executed processing steps such as centrifugation, aliquotation, sample analysis and the like. The term 'laboratory instrument' can cover pre-analytical instruments, post-analytical instruments and also analytical instruments.

The term 'pre-analytical instrument' as used herein can comprise one or more lab-devices for executing one or more pre-analytical processing steps on one or more biological samples, thereby preparing the samples for one or more succeeding analytical tests. A pre-analytical processing step can be, for example, a centrifugation step, a capping-, decapping- or recapping step, an aliquotation step, a step of adding buffers to a sample and the like. The expression 'analytical system' as used herein can encompass any monolithic or multi-modular laboratory device comprising one or more lab-devices or operative units which can be operable to execute an analytical test on one or more biological samples.

The term 'post-analytical instrument' as used herein can encompass any laboratory instrument being operable to automatically process and/or store one or more biological samples. Post-analytical processing steps may comprise a recapping step, a step for unloading a sample from an analytical system, or a step for transporting the sample to a storage unit or to a unit for collecting biological waste.

The term 'analyzer'/'analytical instrument' as used herein can encompass any apparatus or apparatus component configured to obtain a measurement value. An analyzer can be operable to determine via various chemical, biological, physical, optical or other technical procedures a parameter value of the sample or a component thereof. An analyzer may be operable to measure the parameter of the sample or of at least one analyte and return the obtained measurement value. The list of possible analysis results returned by the analyzer can comprise, without limitation, concentrations of the analyte in the sample, a digital (yes or no) result indicating the existence of the analyte in the sample (corresponding to a concentration above the detection level), optical parameters, DNA or RNA sequences, data obtained from mass spectroscopy of proteins or metabolites and physical or chemical parameters of various types. An analytical instrument may comprise units assisting with the pipetting, dosing, and mixing of samples and/or reagents. The analyzer may comprise a reagent-holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The analyzer may comprise a process and detection system whose workflow is optimized for certain types of analysis. Examples of such analyzer can be clinical chemistry analyzers, coagulation chemistry analyzers, immunochemistry analyzers, urine analyzers, nucleic acid analyzers, tissue analyzers (including morphological stainers and histochemical stainers) used to detect the result of chemical or biological reactions or to monitor the progress of chemical or biological reactions.

The term 'laboratory system' as used herein can encompass any system for the use in a laboratory comprising plurality of laboratory instruments operatively connected to a control unit.

The term 'control unit', 'laboratory middleware' as used herein can encompass any physical or virtual processing device configurable to control a laboratory system comprising a plurality of laboratory instruments in a way that workflow(s) and workflow step(s) can be conducted by the laboratory system. The control unit may, for example, instruct the laboratory system (or a specific instrument thereof) to conduct pre-analytical, post analytical and analytical workflow(s)/workflow step(s). The control unit may receive information from a data management unit regarding which steps need to be performed with a certain sample. In some embodiments, the control unit might be integral with a data management unit, may be comprised by a server computer and/or be part of one instrument or even distributed across multiple instruments of the laboratory system. The control unit may, for instance, be embodied as a programmable logic controller running a computer-readable program provided with instructions to perform operations.

The term 'communication network' as used herein can encompass any type of wireless network, such as a WIFI, GSM, UMTS or other wireless digital network or a cable based network, such as Ethernet or the like. In particular, the communication network can implement the Internet protocol IP. For example, the communication network can comprise a combination of cable-based and wireless networks. In embodiments wherein units of the system are comprised within one laboratory instrument, the communication network can comprise communication channels within an instrument.

The term 'user interface' as used herein can encompass any suitable piece of software and/or hardware for interactions between an operator and a machine, including but not limited to a graphical user interface for receiving as input a command from an operator and also to provide feedback and convey information thereto. Also, a system/device may expose several user interfaces to serve different kinds of users/operators.

The term 'workflow' as used herein can refer to a collection of workflow steps/processing steps. According to some embodiments, the workflow can define a sequence in which the processing steps are carried out.

The term 'workflow step' or 'processing step' as used herein can encompass any activity belonging to a workflow. The activity can be of an elementary or complex nature and can typically be performed at or by one or more instrument(s).

The terms 'sample', 'patient sample' and 'biological sample' can refer to material(s) that may potentially contain an analyte of interest. The patient sample can be derived from any biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The patient sample can be pretreated prior to use, such as preparing plasma from blood, diluting viscous fluids, lysis or the like. Methods of treatment can involve filtration, distillation, concentration, inactivation of interfering components, and the addition of reagents. A patient sample may be used directly as obtained from the source or used following a pretreatment to modify the character of the sample. In some embodiments, an initially solid or semi-solid biological material can be rendered liquid by dissolving or suspending it with a suitable liquid medium. In some embodiments, the sample can be suspected to contain a certain antigen or nucleic acid.

A 'STAT sample' can be a sample which needs to be processed and analyzed very urgently as the analysis result may be of life-crucial importance for a patient.

The term 'sample tube' can refer to any individual container for transporting, storing and/or processing a sample. In particular, the term without limitation can refer to a piece of laboratory glass- or plastic-ware optionally comprising a cap on its upper end.

Sample tubes, e.g. sample tubes used to collect blood, can often comprise additional substances such as clot activators or anticoagulant substances, which can have an impact on the processing of the sample. As a consequence, different tube types can typically be adapted for pre-analytical and analytical requirements of a particular analysis, e.g. a clinical chemistry analysis, a hematological analysis or a coagulation analysis. A mix up of sample tube types can make (blood) samples unusable for analysis. To prevent errors in the collection and handling of samples, the sample caps of many tube manufacturers can be encoded according to a fixed and uniform color scheme. Some sample tubes types in addition, or alternatively, can be characterized by particular tube dimensions, cap dimensions, and/or tube color. A dimension of a tube cab comprise e.g. its height, its size and/or further characteristic shape properties.

The term 'sample plate', 'microplate' or 'microwell plate' as used herein can refer to a plate/tray as commonly used in many analytical research and clinical diagnostic testing laboratories having a plurality of sample wells arranged in a rectangular matrix. Each well of a microplate can typically hold between tens of nanolitres to several milliliters of biological sample. Microplates can have various dimensions, formats and configurations. For colorimetric immunoassays, the microplate plate can commonly be formed from a light transmitting plastic since reading of the assay results can typically be done through the contents in the wells. In the case of photon emitting immunoassays, the microplate may be made of opaque plastic, such as black or white polystyrene, in order to reduce "cross-talk" in photometrically reading the results from well to well (i.e. to reduce interference caused by stray photons).

The terms 'aliquot', 'patient sample aliquot' and 'biological sample aliquot' can refer to a portion of the sample, patient sample or biological sample usually obtained by aliquoting, i.e. dividing the biological sample, in particular using a pipetting process. In this context, the biological sample can be referred to as primary sample and the tube in which it resides can be referred to as primary sample tube while the sample portions divided from the primary sample can be called aliquots and the tube(s) in which they reside can be referred to as aliquot tubes or secondary tubes. An aliquot(s) of a biological sample can usually be created into a secondary sample tube or sample plate well separate from the primary sample tube or sample plate well.

The term 'sample rack' can be a carrier, typically made of plastics and/or metal, adapted for receiving, holding and transporting one or more sample tubes, e.g., 5 or more sample tubes, e.g., disposed in one or more rows. Apertures, windows or slits may be present to enable visual or optical inspection or reading of the sample tubes or of the samples in the sample tubes or of a label, such as a barcode, present on the sample tubes held in the sample rack.

The term 'tube type' as used herein can refer to a category of sample tubes which can be characterized by at least one shared property, whereby the shared property can be automatically detected by a lab-device and can thus be used to discriminate a set of sample tubes of a first tube type from another. Some tube types are designed for carrying samples, which can be used for a plurality of different analytical tests. An example for such a tube type is a serum tube. However, a tube type may also be particular for one single analytical test.

The term 'sample input station' as used herein can refer to a part of an instrument or to an entire instrument configured to receive sample tubes before these can be processed by the same instrument or transferred (by a transport system or manually) to another instrument of the laboratory system. The sample tubes may be loaded into the sample input station individually or rackwise.

The workcells may be connected by a transport system (conveyor and/or robotic arm). Alternatively, samples can be transported from one workcell to the other manually or workcells can be directly connected to each other.

The term 'analyte' as used herein can refer to a component of a sample to be analyzed, e.g. molecules of various sizes, ions, proteins, metabolites and the like. Information gathered on an analyte may be used to evaluate the impact of the administration of drugs on the organism or on particular tissues or to make a diagnosis. Thus, 'analyte' is a general term for substances for which information about presence and/or concentration is intended. Examples of analytes are e.g., glucose, coagulation parameters, endogenic proteins (e.g. proteins released from the heart muscle), metabolites, nucleic acids and so on.

The term 'analysis' or 'analytical test' as used herein can encompass a laboratory procedure characterizing a parameter of a biological sample, e.g. light absorption, fluorescence, electrical potential or other physical or chemical characteristics of the reaction to provide the measurement data.

The term 'target' as used herein can refer to any data object, computer loadable data structure, modulated data representing such data being indicative of one or more laboratory processing steps to be executed on a particular biological sample. For example, a target record may be a file or an entry in a database. According to embodiments disclosed herein, a target can indicate a test order for an analytical test if, for example, the target comprises or is stored in association with an identifier of an analytical test to be executed on a particular sample. Alternatively, or additionally, the target may refer to pre- and/or post-analytical processing steps to be performed on the biological sample.

The term 'analytical data' as used herein can encompass any data that is descriptive of a result of a measurement of a biological sample. In case of a calibration, the analytical data can comprise the calibration result, i.e., calibration data. In particular, the analytical data can comprise an identifier of the sample for which the analysis has been performed and data being descriptive of a result of the analysis, such as measurement data.

The terms 'sorting' and 'grouping' in the following can be used synonymously in order to refer to the grouping of biological samples based on features shared by all samples of a particular group for processing all samples of a group in the same manner at least during a subsequent processing step.

The term 'hemolytic' respectively 'hemolysis' can refer to vascular cell damage of a biological sample. Commonly cell damage can occur during phlebotomy; a frequent reason for sample rejection. In vitro hemolysis, which can occur during phlebotomy, causes cell membrane disruption and leakage of hemoglobin into the surrounding fluid. It can occur from improper specimen collection due to a wrong needle, excessive mixing of the blood sample, inadequate storage temperatures or rough handling during specimen transport. As an alternative to rejecting the sample, results may be reported with an alert to clinicians to interpret the results in the presence of hemolysis.

The term 'lipemic' respectively 'lipemia' can refer to plasma that has large lipid particles that include lipoproteins and chylomicrons. As a result, these samples can have increased sample turbidity and may result in the prolongation of coagulation results. Interference can be variable among analyzers. Turbid samples can cause attenuation of the intensity of light passed through a sample due to scatter, reflectance or absorption. Large lipid particles may be removed from samples by ultracentrifugation. The interference of lipemia may also be minimized by using higher dilutions.

The term 'icteric' respectively 'icterus' can refer to plasma samples having high levels of bilirubin. Icteric plasma samples can have a high prevalence in samples from patients in the intensive care unit, as well as gastroenterology, surgical and pediatric patients.

Figure 1B:
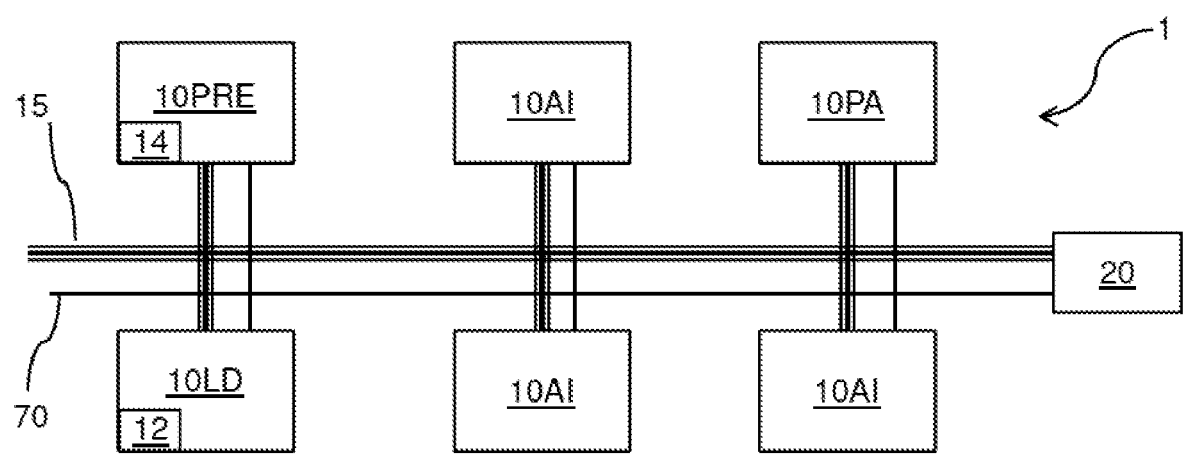
FIG. 1B illustrates a highly schematic block diagram of an embodiment of the disclosed laboratory system comprising pre-, post- and —analytical instruments connected by a sample transportation system according to an embodiment of the present disclosure.

As shown on the block diagram of FIG. 1A, embodiments of the disclosed laboratory system 1 for processing biological sample(s) can comprise a plurality of laboratory instruments 10, 10PRE, 10LD, 10AI, 10PA and a control unit 20 communicatively connected by a communication network 70. The plurality of laboratory instruments 10, 10PRE, 10LD, 10AI, 10PA can be configured to execute processing steps on the biological samples according to instructions from the control unit 20. As shown on FIG. 1B, according to further embodiments of the disclosed laboratory system 1, the plurality of laboratory instruments 10, 10PRE, 10LD, 10AI, 10PA may be one or more instruments from the list comprising pre-analytical instruments 10pre, laboratory instrument(s) for loading samples 10LD comprising a sample input station 12, post-analytical instruments 10PA and also analytical instruments 10AI.

The pre-analytical instruments 10pre comprised by the laboratory system 1 may be one or more from the list comprising: an instrument for centrifugation of samples, a capping-, decapping- or recapping instrument, aliquoter, a buffer to temporarily store biological samples or aliquots thereof.

The post-analytical instruments 10pre comprised by the laboratory system 1 may be one or more from the list comprising: a recapper, an unloader for unloading a sample from an analytical system and/or transporting the sample to a storage unit or to a unit for collecting biological waste.

According to various embodiments of the disclosed laboratory system 1, the plurality of laboratory instruments 10, 10PRE, 10LD, 10AI, 10PA may be identical or different instruments such as clinical—& immunochemistry analyzers, coagulation chemistry analyzers, immunochemistry analyzers, urine analyzers, nucleic acid analyzers, hematology instruments etc.

According to further embodiments, the sample input station 12 and the plurality of laboratory instruments 10, 10PRE, 10LD, 10AI, 10PA can be connected by a transportation system 15 (see FIG. 1B)—such as a conveyor belt transportation system or a multi-dimensional sample tube transportation table—configured to transport sample tubes containing biological samples or aliquots thereof between the sample input station 12 and the plurality of laboratory instruments 10, 10PRE, 10LD, 10AI, 10PA.

The sample input station 12 can be configured to receive biological samples comprised in sample tubes. The sample tubes may be loaded individually or in sample tube racks, each rack capable of holding one or more sample tubes. According to various embodiments of the disclosed laboratory system 1, the sample input station 12 can be comprised within a pre-analytical laboratory instrument 10PRE, comprised within the plurality of laboratory instruments 10, 10PRE, 10LD, 10AI, 10PA or it can be a dedicated laboratory instrument for loading samples 101d. At least one of the laboratory instruments 10, 10PRE, 10LD, 10AI, 10PA, in particular, the laboratory instrument for loading sample 10LD comprising a sample input station 12, can be configured to identify the biological sample. According to a particular embodiment, the sample input station 12 can comprise an identifier reader configured to identify the biological samples based on sample tube identifier(s) associated with the sample tube(s). According to embodiments of the disclosed system, the sample tube identifier can be a bar code or an RFID tag. Correspondingly, the identifier reader can be a barcode reader or an RFID reader.

Figure 2:
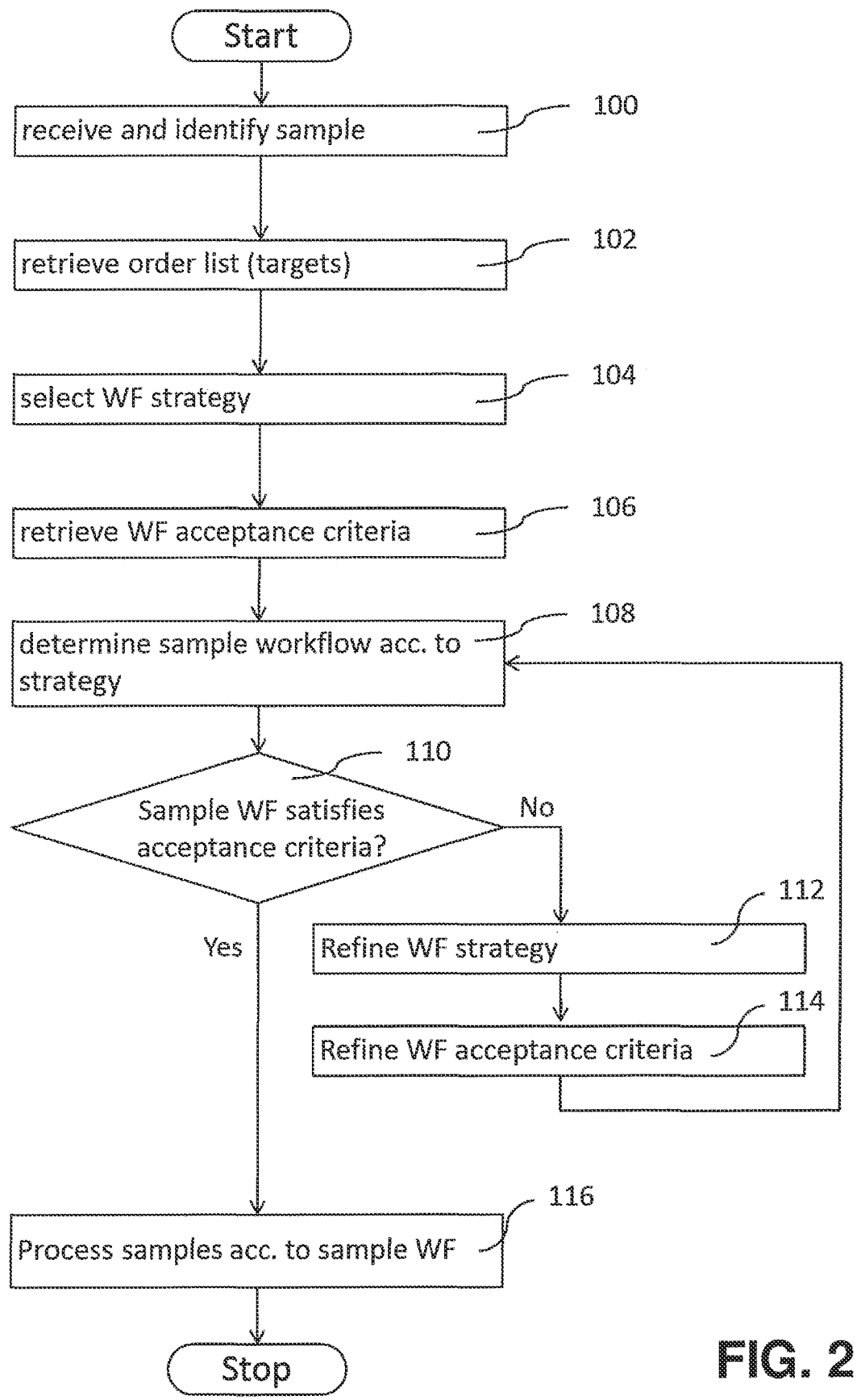
FIG. 2 illustrates a flowchart illustrating the disclosed method for operating a laboratory system according to an embodiment of the present disclosure.

A first embodiment of the method for operating a laboratory system 1 will be now described as illustrated on the flowchart of FIG. 2.

In a step 100, one of the plurality of laboratory instruments 10, 10PRE, 10LD, 10AI, 10PA can receive and identify the biological sample. According to particular embodiments of the disclosed method/system, the biological sample can be identified based on an identification label attached to a sample tube holding the biological sample.

Once the biological sample is identified, in step 102, the control unit 20 can retrieve an order list from a database, the order list comprising a plurality of targets corresponding to the biological sample. Each target can define one or more processing steps to be carried out on the biological sample by one or more of the laboratory instruments 10, 10PRE, 10LD, 10AI, 10PA. According to particular embodiments of the disclosed method/system, several processing steps may be carried out at the same target, such as several aliquots being prepared from the biological sample; or several analytical tests being carried out by the same analytical instrument.

In addition to retrieving the order list comprising a plurality of targets corresponding to the biological sample, according to particular embodiments of the disclosed method/system, in a step 103 the control unit 20 can further be configured to retrieve/determine various properties of the targets comprising one or more of:

- Target priority—representative of an urgency with which a target is to be processed. For example, targets for STAT samples (e.g. emergency care) are prioritized over other targets. According to further embodiments of the disclosed method/system, the control unit 20 can set/adjust the target priority of the plurality of targets based on one or more of:
  - other targets comprised by the order list;
  - a consumable(s) required for performing the processing steps corresponding to the respective target;
  - a work shift of the laboratory system 1; and/or
  - an origin of the respective target (e.g. prioritization of test orders originating from a particular hospital or hospital unit).
- An indicator indicative whether the target is compulsory test or a non-compulsory target
  - This property defines if a target is absolutely mandatory to be carried out or the target may be postponed/discarded if for some reason it cannot be carried out (such as insufficient sample volume) within the current sample workflow. Failure of a workflow to incorporate all compulsory targets would result in rejection of that workflow (see below regarding the "compulsory target priority rule").
- Target sensitivity level—indicative of how sensitive a target is—in particular to cross contamination. For example, analytical instruments performing nucleic acid testing (NAT) are extremely sensitive; therefore have a correspondingly high target sensitivity level. Another aspect that affects the risk of cross contamination can be the history of a biological sample or of a particular aliquot thereof. For example, if a particular aliquot or the primary sample has been processed by a target which uses a multi-use liquid handling needle (instead of disposable pipettes), the same aliquot may not be processed by a target having a higher target sensitivity level as the aliquot could potentially be contaminated.
- Minimum sample volume for the target—This value defines the minimum amount of sample volume that may be required for performing all processing steps according to a particular target.
- Estimated processing time—This value defines the minimum amount of time that is required for performing all processing steps according to a particular target.

In step 104, the control unit 20 can select/determine/retrieve a workflow strategy according to which it will perform the first attempt to determine the sample workflow for processing the biological samples. The workflow strategy can define one or more priority rules in processing the biological sample—see below for a more detailed description of priority rules.

According to various embodiments of the disclosed method/system, the control unit 20 can retrieve the workflow strategy from a database or look up table, which can be stored directly on a storage device of the control unit 20 or a storage device communicatively connected thereto.

Figure 3:
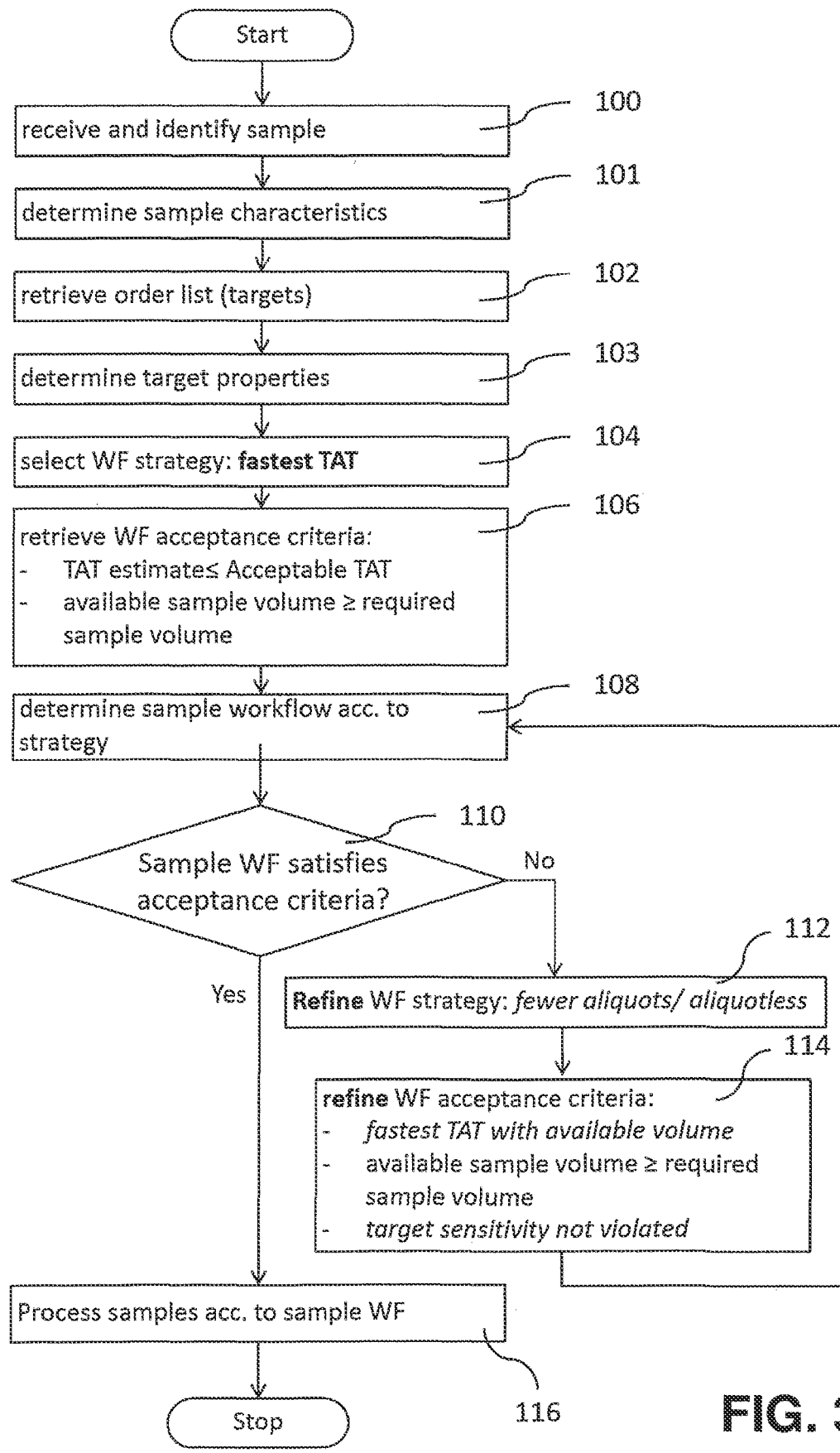
FIG. 3 illustrates a flowchart illustrating the disclosed method for operating a laboratory system according to a further embodiment of the present disclosure.

According to various embodiments of the disclosed method/system, the workflow strategy can comprise one or more of the following priority rules according to which the sample workflow is determined by the control unit 20:

Fastest turn-around-time (TAT) priority rule—A strategy comprising this priority rule will prioritize the processing speed of the sample workflow. According to a first embodiment, processing speed of the sample workflow can be prioritized by increasing the number of aliquots created from the biological sample, thereby enabling simultaneous and/or time-wise overlapping processing of the biological sample respectively aliquots thereof by multiple laboratory instruments 10, 10PRE, 10LD, 10AI, 10PA at a time. Hence, the step of determining a sample workflow based on the workflow strategy can comprise the step of maximizing the number of targets processed in parallel by maximizing the number of aliquots to be created from the biological sample. FIG. 3 shows a flowchart of a further embodiment of the disclosed method for operating a laboratory system 1 illustrating a workflow strategy comprising the fastest turn-around-time (TAT) priority rule.

Figure 4:
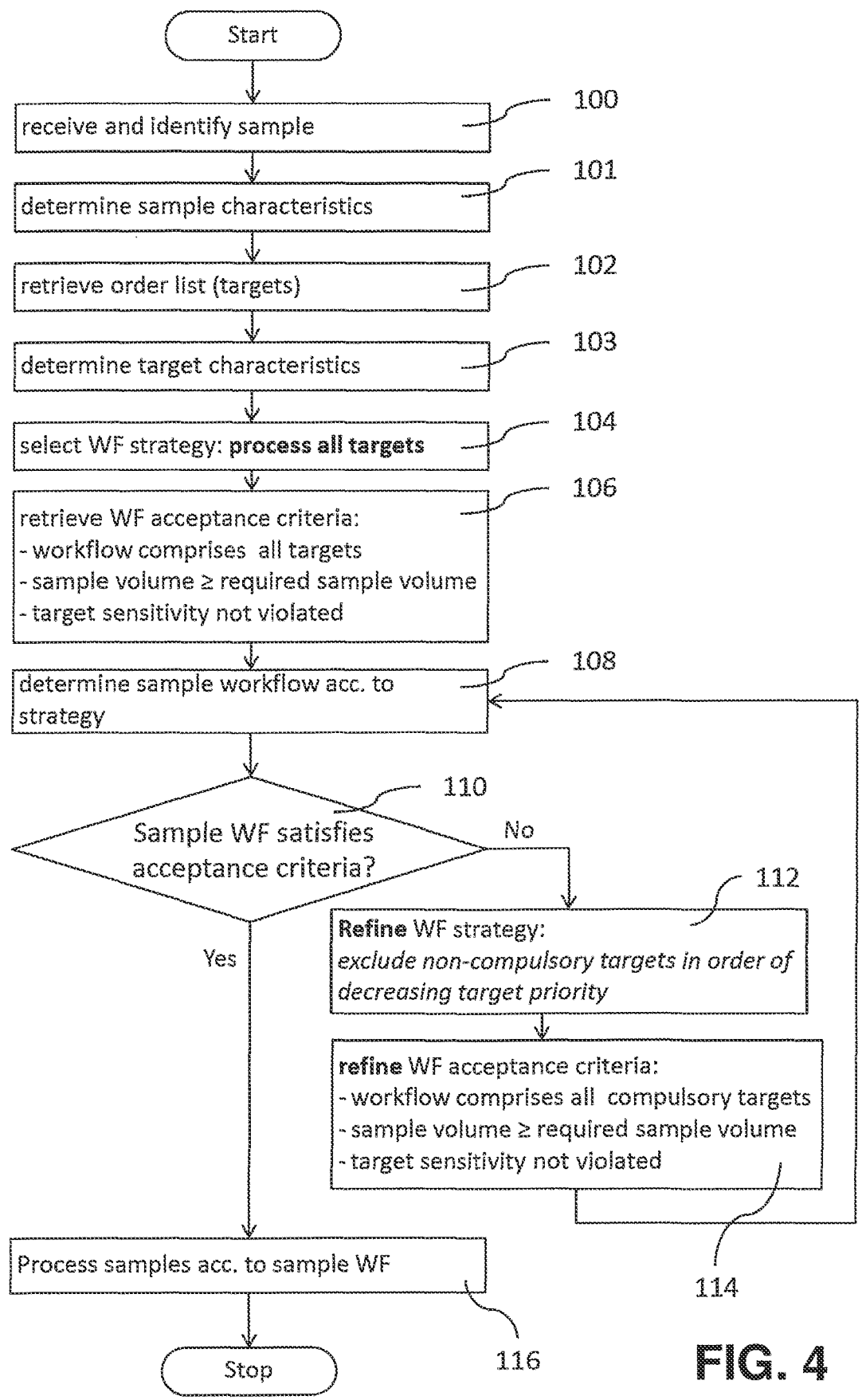
FIG. 4 illustrates a flowchart illustrating the disclosed method for operating a laboratory system according to yet another embodiment of the present disclosure.

All targets complete priority rule—A strategy comprising this priority rule aims to determine a sample workflow enabling the processing of all targets on the order list. Such workflow strategy will prioritize completeness of the workflow over e.g. processing speed. Hence, this strategy can determine a workflow based on fewer aliquots or a completely aliquot-less workflow (if target contamination sensitivity is not violated) to ensure all targets are processed based on the available biological sample, in particular based on the available sample volume. On the other hand, if the available sample volume is sufficient but the biological sample must be processed quickly to avoid degradation of the sample (e.g. coagulation testing), then this workflow strategy can balance the number of aliquots created for timely processing and the amount of available sample volume. FIG. 4 shows a flowchart of an even further embodiment of the disclosed method for operating a laboratory system illustrating a workflow strategy comprising the process all targets priority rule.

Least consumable waste priority rule—A strategy comprising this priority rule aims to align the timing of processing of the targets with a schedule of tests performed by the corresponding laboratory instrument 10, 10PRE, 10LD, 10AI, 10PA and/or a validity of quality control of respective assay of the corresponding laboratory instrument. For example, there are laboratory instruments 10, 10PRE, 10LD, 10AI, 10PA that can be able to process multiple samples in parallel (in a batch). In such case, according to embodiments of the disclosed method/system, a strategy comprising the "Least consumable waste" priority rule can take into consideration which processing steps are already scheduled to be carried out so as to align the timing of the processing of the identified biological sample or aliquots thereof with the already scheduled processing to enable parallel processing, thereby saving consumables such as multiwell sample plates(s) and/or control/calibrator material.

Compulsory target priority rule—A strategy comprising this priority rule aims to prioritize the processing of targets identified as compulsory targets. In particular, the use of the available sample volume of the biological sample can be taken in consideration to ensure that the sample workflow can accommodate at least all of the compulsory targets with the available sample volume.

It can be noted that a workflow strategy may comprise more than one priority rules, in particular ordered by relevance for the particular workflow strategy. Hence, according to a further embodiment of the disclosed method/system, the workflow strategy can comprise as first priority the "all targets complete priority rule" combined with the "fastest turn-around-time (TAT) priority", which in combination result in a workflow strategy which can determine a sample workflow which can have the fastest TAT but at the same time create just as many aliquots for simultaneous processing so that the available sample volume suffices for completing all targets.

Once the workflow strategy has been selected, in step 106, the control unit 20 can retrieve the corresponding workflow acceptance criterion from a database. According to various embodiments of the disclosed method/system, the control unit 20 can retrieve the workflow acceptance criterion from a database or look up table, which can be stored directly on a storage device of the control unit 20 or a storage device communicatively connected thereto. The workflow acceptance criterion can define the conditions, which the sample workflow will have to meet/satisfy in order for the sample workflow to be considered acceptable.

According to embodiments of the disclosed method/system, the workflow acceptance criterion can comprise one or more of the following workflow evaluation rule(s):

Determining whether an estimate of the total turn-around-time (TAT) of the sample workflow is lower than or equal to a predefined acceptable TAT.

According to embodiments disclosed herein, in order to estimate the total turn-around-time, the control unit 20 can retrieve the estimated processing time corresponding to each processing step of each target in the order list. Thereafter, the control unit 20 can compute the total turn-around-time (TAT), taking into consideration that certain targets can be processed using aliquots of the biological sample in parallel.

Determining whether an estimate of the total required sample volume is lower than or equal to the available sample volume of the biological sample.

According to embodiments disclosed herein, in order to estimate the total required sample volume, the control unit 20 can retrieve the estimated required sample volume corresponding to each processing step of each target in the order list. Thereafter, the control unit 20 can compute the estimate total required sample volume, taking into consideration that the creation of each aliquot from the biological sample commonly can result in a waste of sample volume due to "dead volume" in various sample containers. Furthermore, according to certain embodiments, the control unit 20 can be configured to reserve a predetermined reserve volume of the biological sample, the reserve volume not being considered for determining the sample workflow based on the workflow strategy and the order list, wherein the reserve volume can be kept for future targets and/or for archiving purposes. In such cases, the estimate total required sample volume can comprise this reserve volume.

Determining whether target sensitivity is not violated, wherein target sensitivity can be violated if a target of higher sensitivity is scheduled in the sample workflow to be performed on an aliquot (or primary sample) after a target of a lower sensitivity has performed a processing step on the same aliquot (or primary sample). According to embodiments disclosed herein, in order to determine if target sensitivity is not violated, the control unit 20 can be configured to retrieve a target sensitivity level of each target, wherein the target sensitivity level can be indicative of how sensitive a target is, e.g. to cross contamination. For example, analytical instruments performing nucleic acid testing (NAT) are extremely sensitive; therefore, they can have a correspondingly high target sensitivity level. Another aspect that affects the risk of cross contamination is the history of a biological sample or of a particular aliquot thereof. For example, if a particular aliquot or the primary sample has been processed by an instrument which uses a multi-use liquid handling needle (instead of disposable pipettes), the same aliquot may not be processed by a target having a higher target sensitivity level as the aliquot could potentially be contaminated. To summarize, target sensitivity can be determined by the type of analytical test of the target and/or by the methodology of handling the biological sample/aliquot.

According to embodiments of the disclosed method/system, the workflow acceptance criterion can comprise a plurality of workflow evaluation rules which can be combined by one or more logical operators, e.g., AND, OR, XOR, NOT, and the like.

According to embodiments disclosed herein, there are two kinds of workflow evaluation rules:
  workflow acceptance rules, which must be satisfied; and
  workflow rejection rules, which must not be violated by a sample workflow.

Nevertheless, in most cases, workflow rejection rules and workflow acceptance rules can be exchanged using the corresponding logical operators.

According to one embodiment, the workflow acceptance criterion can be defined as follows:
  workflow evaluation rule a) is an estimate of the total turn-around-time (TAT) of the sample workflow lower than or equal to a predefined acceptable TAT?"AND"
  workflow evaluation rule b) is the estimate of the total required sample volume lower than or equal to the available sample volume of the biological sample?"AND"
  workflow evaluation rule c) is target sensitivity not violated?

Hence the sample workflow is acceptable if it satisfies the workflow acceptance criterion, which in this embodiment, requires that workflow evaluation rules a), b) and c) are all satisfied.

According to embodiments herein disclosed, the control unit 20 can be configured to determine characteristics of the biological sample—step 101, comprising one or more of:
  Sample Volume of the Biological Sample.
  The sample volume can be determined using liquid level detection and/or by retrieving the volume of the biological sample from a database (where it was registered either manually or determined by any method of liquid level detection and saved in the database).
  Sample Quality of the Biological Sample.
  Sample quality can be very important, in particular, in analytical processing steps of the biological sample. According to embodiments of the disclosed method/system, sample quality can be determined by a pre-analytical instrument 10PRE, such as by imaging or other suitable sample quality determining methods. Common sample quality characteristics can be indicative whether the biological sample is hemolytic, icteric or lipemic.
  Sample Collection Date and Time.
  The date and time a sample has been collected can play an important role in the accuracy of an analytical processing step of targets. In particular, coagulation testing, as well as hematological instruments, can be greatly affected by an aging sample. According to embodiments disclosed herein, sample workflows can be determined by the control unit in view of sample collection date and time as well as a target sensitivity to sample aging.
  Indications Identifying the Patient.
  Often it may be desired that all targets of an order list belonging to a particular patient are completed simultaneously in order to facilitate comprehensive diagnoses of that patient with all results at hand. Thus, according to embodiments disclosed herein, sample workflows can be determined by the control unit in view of the indications identifying the patient.

Sample Processing History.

In this context, sample history can refer to an indication as to how the sample may have been affected by previously performed processing steps. In particular, potential contamination of the sample by a laboratory instrument can be comprised within the sample history. According to embodiments disclosed herein, sample workflows can be determined by the control unit in view of the sample history as well as the target sensitivity level.

According to embodiments disclosed herein, the workflow acceptance criterion can comprise one or more workflow evaluation rule(s) based on one or more characteristics of the biological sample.

After retrieving the order list, selecting the workflow strategy, and retrieving the corresponding workflow acceptance criterion, in step 108, the control unit 20 can determine a sample workflow.

According to embodiments of the disclosed method/system, the sample workflow can define one or more of:

A number n of aliquots to be prepared from the biological sample. This number n can define into how many portions the biological sample can be divided; such portions can be referred to as aliquots of the biological sample. The biological sample as received can then be referred to as primary sample. According to certain embodiments, the control unit 20 can be configured to reserve a predetermined reserve volume of the biological sample, the reserve volume not being considered for determining the sample workflow based on the workflow strategy and the order list, wherein the reserve volume can be kept for future targets and/or for archiving purposes. Depending on the workflow strategy selected, the number of aliquots may be even 0—in other words no aliquots are created and all processing steps of all targets are performed on the primary sample. Such workflow can also be referred to as aliquotless workflow. It can be noted that while an aliquotless sample workflow is feasible for certain order lists, this may not always be the case due to risk of cross-contamination. In particular, there can be a risk that one laboratory instrument contaminates the biological sample and therefore another—more sensitive—laboratory instrument can no longer provide precise analytical results due to the risk that the biological sample has been contaminated. In such case, the workflow strategy does not satisfy at least one workflow evaluation rule related to cross-contamination and a new sample workflow can be determined after refining the workflow strategy wherein an aliquot can be created and allocated to the more sensitive target. Alternatively, or in addition, the refined workflow strategy can determine a sample workflow wherein the more sensitive target can be performed first on the same aliquot (or primary sample) and the less sensitive thereafter.

Allocation of an aliquot or primary sample to each target. Once the required number n of aliquots has been determined (could be 0 as mentioned above), an aliquot or the primary sample can be allocated to each target for performing the one or more processing steps at the target.

Sequence in which the targets are to be processed. The target processing sequence can define the order in which the biological sample is processed by the targets. The sequence can be of great importance especially when the same aliquot or primary sample is processed by more than one laboratory instruments of different sensitivity and/or contamination risk.

Timing of processing of the targets. According to embodiments of the disclosed method/system, in addition to the processing sequence, the timing according to which the biological sample or aliquots thereof are processed can be also defined by the sample workflow. For example, the timing can be of great importance if the biological sample first needs to be prepared by a pre-analytical instrument 10PRE and must be processed by an analytical instrument 10AI immediately thereafter. Another example can be when the biological sample needs to spend a very specific amount of time in a pre-analytical instrument 10PRE such as an incubator or centrifuge to ensure proper sample preparation for an analytical instrument 10AI. Furthermore, the timing of the processing of the targets can also relevant in view of sample degradation which is often correlated with its processing time, especially when the sample is outside of a temperature controlled area, in which case the sample can be transferred to a post-analytical instrument 10PA such as a temperature-controlled archiving unit after a certain amount of time. Another example is when certain processing steps, in particular, certain rarely performed analytical tests are performed relatively rarely in a laboratory system 1. In such cases, embodiments of the disclosed method/system can align the timing of processing of the targets with a schedule of tests performed by the laboratory system 1 in order to avoid that the respective target cannot be performed for an extended period of time.

Timing of processing of the targets can also be of great importance in view of the validity of quality control and/or calibration of certain laboratory instruments 10, 10PRE, 10LD, 10AI, 10PA, in particular, analytical instruments 10AI.

A list of excluded targets. The list of excluded targets can comprise all targets not comprised by the sample workflow in case no sample workflow can be determined which satisfies the workflow acceptance criterion and comprises all targets.

As illustrated on FIGS. 2 through 4, as a next step 110, the control unit 20 can determine whether the sample workflow satisfies the workflow acceptance criterion. According to embodiments of the disclosed method/system where the workflow acceptance criterion can comprise a plurality of workflow evaluation rules which can be combined by one or more logical operators, the workflow criterion as a logical combination of workflow evaluation rules can be evaluated. The term 'satisfy/satisfies' can refer to the fact that applying the logical combination of the workflow evaluation rules on the sample workflow can result in a "true" statement.

If the sample workflow satisfies the workflow acceptance criterion, in step 116, the control unit 20 can instruct the laboratory instruments 10, 10PRE, 10LD, 10AI, 10PA to process the biological sample according to the sample workflow. Corresponding to the targets in the order list and the sample workflow determined by the control unit 20, the plurality of the laboratory instruments 10, 10PRE, 10LD, 10AI, 10PA can be instructed to carry out pre-, post- and analytical processing steps on the biological sample and/or aliquots thereof.

However, if the sample workflow does not satisfy the workflow acceptance criterion, the control unit 20 can be configured to refine the workflow strategy—step 112; refine the workflow acceptance criterion—step 114 and determine the sample workflow again—step 108—based on the (refined) workflow strategy and the order list until the sample workflow satisfies the (refined) workflow acceptance criterion.

According to the disclosed method/system, refining the workflow strategy can comprise a change in at least one of the one or more priority rules in processing the biological sample such as:

refining the sequence in which the targets are to be processed; and/or refining the timing of processing of the targets; and/or refining the list of excluded targets not comprised by the sample workflow, if a sample workflow cannot be determined which satisfies the workflow acceptance criterion and comprises all targets; and/or refining the number n of aliquots to be prepared from the biological sample; and/or refining the allocation of an aliquot or primary sample to each target.

Corresponding to the "all targets complete priority rule", the step 112 of refining the workflow strategy can comprise reducing the number of aliquots to be created from the biological sample until an estimate of the total required sample volume for all targets is lower than or equal to the available sample volume of the biological sample. Alternatively, or in addition, the step 112 of refining the work flow strategy can comprise allocating a target comprising an analytical processing step to an analytical instrument 10AI which can require a lower amount of sample volume (e.g. thanks to different hardware, different dilution level).

Corresponding to the "fastest TAT priority rule", the step 112 of refining the workflow strategy can comprise allocating a target comprising an analytical processing step to an analytical instrument 10AI which can have a lower estimated processing time.

Corresponding to the "compulsory target priority rule", the step 112 of refining the workflow strategy can comprise excluding non-compulsory targets from the sample workflow if the available sample volume of the biological sample is less than an estimate of the total required sample volume for all targets.

According to the disclosed method/system, the step 114 of refining the workflow acceptance criterion can comprise a change in at least one of the workflow evaluation rule(s), wherein the workflow evaluation rule(s) can be refined in view of the priority rule(s) of the workflow strategy.

Corresponding to the "all targets complete priority rule", the step 114 of refining the workflow acceptance criterion can comprise the step of increasing the acceptable estimated TAT.

Corresponding to the "compulsory target priority rule", the step 114 of refining the workflow acceptance criterion can comprise the step of excluding non-compulsory target from the workflow evaluation rules, thereby prioritizing compulsory targets over non-compulsory targets.

According to embodiments disclosed herein, the step 112 of refining the workflow strategy and/or the step 114 of refining the workflow acceptance criterion can be in accordance with workflow evaluation rule(s) not satisfied by the sample workflow of the preceding iteration. In other words, if a workflow evaluation rule is not satisfied, the workflow strategy can be refined in the next iteration so as to no longer violate that criterion. If, however, this is not possible, the workflow evaluation rule can also be refined, this refining often resulting in the workflow evaluation rule being more permissive, i.e. less strict. For example, fastest TAT priority rule, the more permissive workflow evaluation rule can allow for a higher acceptable processing time.

According to further embodiments, the steps 112 refining workflow strategy; 114—refining workflow acceptance criterion and step 108 of determining the sample workflow can be performed at most for a predetermined maximum number of iterations. If even after this predetermined maximum number of iterations (attempts), the sample workflow still does not satisfy the workflow acceptance criterion, the control unit 20 can control the laboratory system 1 to:

route the biological sample to an error target and/or generate a signal indicative of an error in determining a sample workflow; and/or create empty aliquot tubes with corresponding sample tube identifiers and generate a signal indicative of an instruction to an operator to provide additional sample volume into the empty aliquot tubes; and/or create as many aliquots of the biological sample as possible based on the available sample volume and route a sample tube comprising the primary sample to an error target and generate a signal indicative of an instruction to an operator to provide additional sample volume and/or generate an alarm signal indicative that the sample workflow does not satisfy the workflow acceptance criterion after the maximum number of iterations.

In this context, iteration can refer to the series of steps: 104—selecting/refining the workflow strategy; 106—retrieving/refining workflow acceptance criterion, and 108—determining/re-determining the sample workflow.

Further disclosed and proposed is a computer program including computer-executable instructions for performing the method according to the present disclosure in one or more of the embodiments enclosed herein when the program is executed on a computer or computer network. Specifically, the computer program may be stored on a computer-readable data carrier. Thus, specifically, one, more than one or even all of method steps as indicated above may be performed by using a computer or a computer network, preferably by using a computer program.

Further disclosed and proposed is a computer program product having program code, in order to perform the method disclosed herein in one or more of the embodiments enclosed herein when the program is executed on a computer or computer network. Specifically, the program code may be stored on a computer-readable data carrier.

Further disclosed and proposed is a data carrier having a data structure stored thereon, which, after loading into a computer or computer network, such as into a working memory or main memory of the computer or computer network, may execute the method according to one or more of the embodiments disclosed herein.

Further disclosed and proposed is a computer program product with program code stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Further disclosed and proposed is a modulated data signal, which contains instructions readable by a computer system or computer network, for performing the method according to one or more of the embodiments disclosed herein.

Referring to the computer-implemented aspects, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Furthermore, hereby disclosed and proposed are:

A computer or computer network comprising at least one processor, wherein the processor can be adapted to perform the method according to one of the embodiments described in this description, a computer loadable data structure that can be adapted to perform the method according to one of the embodiments described in this description while the data structure can be executed on a computer, a computer program, wherein the computer program can be adapted to perform the method according to one of the embodiments described in this description while the program is being executed on a computer, a computer program comprising a program for performing the method according to one of the embodiments described in this description while the computer program is being executed on a computer or on a computer network, a computer program comprising a program according to the preceding embodiment, wherein the program can be stored on a storage medium readable to a computer, a storage medium, wherein a data structure is stored on the storage medium and wherein the data structure is adapted to perform the method according to one of the embodiments described in this description after having been loaded into a main and/or working storage of a computer or of a computer network, and a computer program product having a program code, wherein the program code can be stored or stored on a storage medium, for performing the method according to one of the embodiments described in this description, if the program code is executed on a computer or on a computer network.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A computer implemented method for operating a laboratory system, wherein the laboratory system comprises a plurality of laboratory instruments for processing biological samples and a control unit communicatively connected by a communication network, the method comprising:

receiving and identifying a biological sample by one of the plurality of laboratory instruments;

retrieving an order list from a database by the control unit, the list comprising a plurality of targets corresponding to the biological sample, each of the plurality of targets defining at least one processing step(s) to be carried out on the biological sample by at least one of the plurality of the laboratory instruments;

selecting a workflow strategy by the control unit, wherein the workflow strategy defines at least one priority rule(s) in processing the biological sample;

retrieving workflow acceptance criterion by the control unit from a database corresponding to the workflow strategy;

determining a sample workflow by the control unit for processing the biological sample based on the workflow strategy and the order list;

determining by the control unit whether the sample workflow satisfies the workflow acceptance criterion; and in response to determining that the sample workflow does not satisfy the workflow acceptance criterion, refining workflow strategy by the control unit and determining the sample workflow by the control unit based on the workflow strategy and the order list until the sample workflow satisfies the workflow acceptance criterion.

2. The computer implemented method for operating a laboratory system according to claim 1, further comprising, transporting the biological samples between a sample input station and the plurality of laboratory instruments by a transportation system connected to the sample input station and the plurality of laboratory instruments.

3. The computer implemented method for operating a laboratory system according to claim 2, wherein the sample input station is configured to receive biological samples comprised in sample tubes.

4. The computer implemented method for operating a laboratory system according to claim 1, wherein the biological sample is identified based on an identification label attached to a sample tube comprising the biological sample.

5. The computer implemented method for operating a laboratory system according to claim 1, wherein the identification label is a bar code or RFID tag.

6. The computer implemented method for operating a laboratory system according to claim 1, wherein the sample workflow further defines number n of aliquots to be prepared from the biological sample and allocation of an aliquot or primary sample to each target.

7. The computer implemented method for operating a laboratory system according to claim 6, wherein the workflow strategy comprises at least one of the following priority rules: a fastest TAT priority rule, wherein the strategy comprises the step of maximizing the number of targets processed in parallel by maximizing the number of aliquots to be created from the biological sample, an all targets complete priority rule, wherein the step of refining the workflow (WF) strategy comprises reducing the number of aliquots to be created from the biological sample until an estimate of the total required sample volume for all targets is lower than or equal to the available sample volume of the biological sample, least consumable waste priority rule, wherein the strategy comprises the step of aligning the timing of processing of the targets with a schedule of tests performed by the corresponding laboratory instrument and/or a validity of quality control of respective assay of the corresponding laboratory instrument, and/or compulsory target priority rule, wherein the step of refining the work flow strategy comprises excluding non-compulsory targets from the sample workflow in response to determining that the available sample volume of the biological sample is less than an estimate of the total required sample volume for all targets, thereby prioritizing compulsory targets over non-compulsory targets.

8. The computer implemented method for operating a laboratory system according to claim 7, wherein the workflow strategy comprises as first priority the all target complete priority rule combined with the fastest TAT priority rule.

9. The computer implemented method for operating a laboratory system according to claim 1, wherein the control unit stores the database directly in a storage device of the control unit.

10. The computer implemented method for operating a laboratory system according to claim 1, wherein the database is stored in a storage device communicatively connected to the control unit.

11. The computer implemented method for operating a laboratory system according to claim 1, wherein the steps of refining workflow strategy and determining the sample workflow are performed at most for a predetermined maximum number of iterations and wherein, in response to determining that the sample workflow does not satisfy the workflow acceptance criterion after the maximum number of iterations, the control unit controls the laboratory system to: route the biological sample to an error target and/or generate a signal indicative of an error in determining a sample workflow and/or create empty aliquot tubes with corresponding sample tube identifiers and generate a signal indicative of an instruction to an operator to provide additional sample volume into the empty aliquot tubes and/or to create as many aliquots of the biological sample as possible based on the available sample volume and route a sample tube comprising the primary sample to an error target and generate a signal indicative of an instruction to an operator to provide additional sample volume and/or to generate an alarm signal indicative that the sample workflow does not satisfy the workflow acceptance criterion after the maximum number of iterations.

12. The computer implemented method for operating a laboratory system according to claim 1, further comprising, in response to determining that the sample workflow does satisfy the workflow acceptance criterion, the control unit instructs the plurality of laboratory instruments to process the biological sample according the sample workflow.

13. The computer implemented method for operating a laboratory system according to claim 1, further comprising, determining the characteristics of the biological sample by the control unit.

14. The computer implemented method for operating a laboratory system according to claim 13, wherein the workflow acceptance criterion comprises one or more workflow evaluation rules based on one more characteristics of the biological sample.

15. The computer implemented method for operating a laboratory system according to claim 1, wherein the workflow acceptance criterion comprises one or more workflow evaluation rules combined by one or more logical operators.

16. The computer implemented method for operating a laboratory system according to claim 1, wherein the order list comprises at least one test order.

17. The computer implemented method for operating a laboratory system according to claim 1, wherein the plurality of laboratory instruments comprises at least one analytical instrument.

18. The computer implemented method for operating a laboratory system according to claim 17, wherein the at least one processing step to be carried out on the biological sample comprises at least one analytical test performed by the at least one analytical instrument.

19. The computer implemented method for operating a laboratory system according to claim 1, wherein refining the work flow strategy comprises a change in at least one of the priority rules in the rules of processing the biological sample.

20. The computer implemented method for operating a laboratory system according to claim 1, wherein the workflow acceptance criterion defines conditions which the sample workflow will have to meet in order for the sample workflow to be considered acceptable.

21. The computer implemented method for operating a laboratory system according to claim 1 wherein, in response to determining that the sample workflow does not satisfy the workflow acceptance criterion:
refining the workflow acceptance criterion until the sample workflow satisfies the acceptance criterion; or
generating a signal indicating an error after a predetermined number of iterations of refining the workflow acceptance criterion fails to result in the sample workflow satisfying the workflow acceptance criterion.

* * * * *